United States Patent [19]

Cousse et al.

[11] 4,058,558
[45] Nov. 15, 1977

[54] AROMATIC KETO ACIDS AND DERIVATIVES HAVING ANALGETIC, ANTIINFLAMMATORY, AND HYPOCHOLESTEROLEMIZING ACTION

[75] Inventors: Henri Cousse; Gilbert Mouzin; Jean-Pierre Rieu, all of Castres, France

[73] Assignee: Pierre Fabre S.A., Paris, France

[21] Appl. No.: 560,946

[22] Filed: Mar. 21, 1975

[30] Foreign Application Priority Data

Feb. 17, 1975 France .............................. 75.04912

[51] Int. Cl.² .................... C07C 63/33; A61K 31/19
[52] U.S. Cl. ............................. 260/515 A; 260/544; 260/176; 260/174; 260/501.14; 260/515 R; 260/520 R; 260/520 C; 260/521 R; 260/521 H; 260/558 P; 424/248.54; 424/308; 424/316; 424/317; 424/324; 560/53; 560/51
[58] Field of Search .................. 260/515 R, 515 A

[56] References Cited

U.S. PATENT DOCUMENTS

| 2,130,989 | 12/1935 | Schimmelschmidt | 260/514 R |
| 2,654,778 | 5/1950 | Burtner | 260/520 R |
| 3,182,061 | 5/1965 | Goldschmidt | 260/515 A |
| 3,754,021 | 8/1973 | Shen et al. | 260/515 A |

FOREIGN PATENT DOCUMENTS

2,047,806   4/1972   Germany ........................ 260/515 R

OTHER PUBLICATIONS

Fateen et al., J. of Chem. of United Arab Republic, vol. 10, No. 3, pp. 331-338, (1967).
Helmut et al., Chem. Abstracts, vol. 78, 3969u, (1973).

*Primary Examiner*—James O. Thomas, Jr.
*Assistant Examiner*—G. T. Breitenstein
*Attorney, Agent, or Firm*—Gordon W. Hueschen

[57] ABSTRACT

This invention relates to new chemical compounds useful as drugs, as well as to pharmaceutical compositions containing the same.

The new products are aromatic keto acid compounds with antiinflammatory as well as analgetic and hypocholesteremic activity and having the general formula

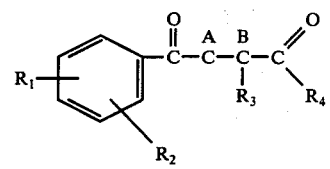

wherein $R_1$ is hydrogen, halogen, phenyl, halophenyl, phenoxy, or substituted phenoxy.

$R_2$ is hydrogen or alkoxy.

$R_1$ and $R_2$ may form a ring, for instance: phenyl or cyclohexyl.

$R_3$ is always other than hydrogen, being either methyl ($CH_3$) or methylene. When $R_3$ is $CH_3$, a double bond is present between the A and B carbons. When $R_3$ is a methylene connected by a double bond to the B carbon, there can be only a single bond between the A and B carbons. The remaining valences of the A carbon atom are satisfied by hydrogen atoms.

$R_4$ may be OH, alkoxy,

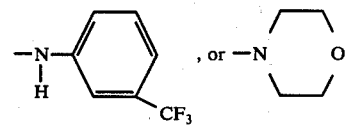

The drugs containing these active principles are useful in the prevention and treatment of inflammatory syndromes, pain, and conditions involving excess cholresterol.

1 Claim, No Drawings

AROMATIC KETO ACIDS AND DERIVATIVES HAVING ANALGETIC, ANTIINFLAMMATORY, AND HYPOCHOLESTEROLEMIZING ACTION

The present invention relates to new keto acids which can be used in therapy.

They are useful in particular as drugs of analgetic, antiinflammatory, and hypocholesteremic action.

The invention also relates to pharmaceutical compositions, which may contain these new compounds or their therapeutically acceptable salts, and which compositions may be administered orally, rectally, or parenterally.

The new compounds have the general formula

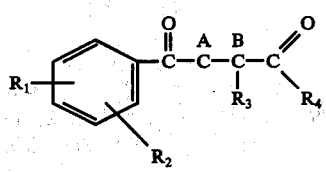

wherein $R_1$ is hydrogen, halogen, phenyl, halophenyl, phenoxy, or substituted phenoxy.

$R_2$ is hydrogen or alkoxy.

$R_1$ and $R_2$ may form a ring, for instance: phenyl or cyclohexyl.

$R_3$ is always other than hydrogen, being either methyl ($CH_3$) or methylene. When $R_3$ is $CH_3$, a double bond is present between the A and B carbons. When $R_3$ is a methylene connected by a double bond to the B carbon, there can be only a single bond between the A and B carbons. The remaining valences of the A carbon atom are satisfied by hydrogen atoms.

$R_4$ may be OH, alkoxy,

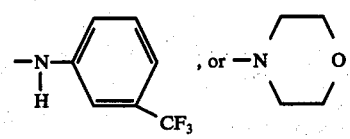

A. The molecules of the formula

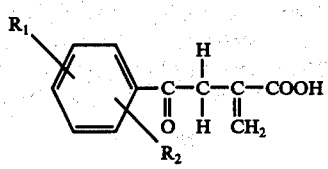

are preferred and are obtained by the action of itaconic anhydride on aromatic substrates in the presence of a Lewis acid catalyst, this being an acylation reaction of the Friedel and Crafts type.

The reaction mechanism is as follows:

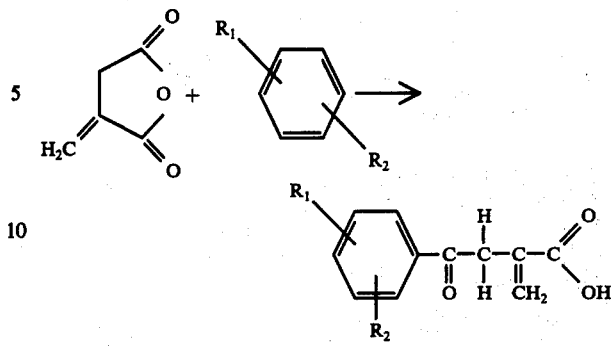

The following chemical compounds and thier method of preparation are given by way of nonlimitative examples (for the sake of convenience, each being designated by a code name):

Example 1.

2-methylene 4-oxo 4-(para cyclo hexyl phenyl) butyric acid ($R_1$ = cyclohexyl) (F 1353)

1 mole of itaconic anhydride and 1 mole of phenyl cyclohexane are dissolved in 500 cc of nitrobenzene.

The reaction mixture is cooled to about 0° C.

One and a half mole of aluminum chloride dissolved in nitrobenzene is then slowly added.

After several hours at room temperature the catalyst is destroyed by a concentrated solution of hydrochloric acid. After elimination of the nitrobenzene, the water-immiscible oily residue is recovered. This residue is crystallized by treatment in a mixture of petroleum ether and benzene.

These crystals may be recrystallized from ethyl alcohol at 80° G.L.

Filter and dry.

The product obtained has the formula:

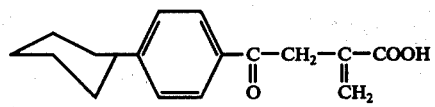

Empirical formula: $C_{17}H_{20}O_3$
Molecular weight: 272.3
Melting Point: 150° C.
Strawyellow crystals
Plate chromatography
  -support: silica
  -solvent: acetic acid/dioxane/benzene 2/8/90
  -development: ultraviolet lamp
  -Rf: 0.43
Solubility properties: insoluble in water.

3% soluble in ethyl alcohol, 1% soluble in water by addition of sodium bicarbonate; 20% soluble in dimethyl acetamide; and 1% soluble in propylene glycol.

EXAMPLE 2.

2-methylene 4-oxo 4-phenyl butyric acid ($R_1$ = H) (F-1350)

From itaconic anhydride treated with a large excess of benzene in the presence of aluminum chloride, there is recovered with a yield of about 70% the derivative of the formula:

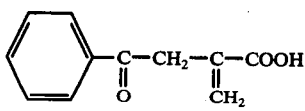

Empirical formula: $C_{11}H_{10}O_3$
Molecular weight: 190.2
White crystals
Melting point: 163° C
Plate chromatography:
 -support: silica gel
 -solvent: acetic acid/dioxane/benzene 2/8/90
 -development: ultraviolet lamp
 -Rf: 0.48
Infrared spectrum: presence of acid and ketone $\nu_{C=O}$ bands at 1700 and at 1680 cm$^{-1}$.
Solubility properties: insoluble in water.
1% soluble in the form of sodium salt; 3% soluble in ethyl alcohol; 10% soluble in dimethyl acetamide; 25% soluble in dimethyl sulfoxide and 6% soluble in acetone.

EXAMPLE 3.

2-methylene 4-oxo 4-(para chloro phenyl) butyric acid ($R_1 = Cl$) (F 1352)

Using chlorobenzene as aromatic substrate and as solvent, by the action of itaconic anhydride in the presence of aluminum chloride there is obtained, after the customary treatment:

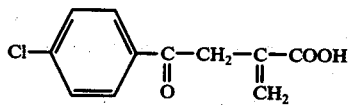

Empirical formula: $C_{11}H_9ClO_3$
Molecular weight: 224.6
Yellow crystals
Melting point: 180° C
Plate chromatography:
 -support: silica gel
 -solvent: acetic acid/dioxane/benzene 2/8/90
 -development: ultraviolet lamp
 -Rf: 0.46
Infrared spectrum: acid and ketone $\nu_{C=O}$ absorption bands at 1700 and 1600 cm$^{-1}$.
Solubility properties: insoluble in water. 1% soluble in form of sodium salt; 3% soluble in ethyl alcohol; 25% soluble in N-methyl pyrrolidone.

EXAMPLE 4.

2-methylene 4-oxo 4-(para phenoxy phenyl) butyric acid

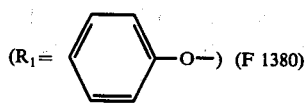

The reaction mixture formed of:
-1 mole of itaconic anhydride
-1 mole of diphenyloxide
-2 moles of $ALCl_3$
in one liter of nitrobenzene is agitated at room temperature for 100 hours; the catalyst is destroyed by concentrated hydrochloric acid in the presence of ice.

The organic phase is treated with $Na_2CO_3$, extracted with methylene chloride and acidified. The white crystals obtained in a yield of about 80% have the formula:

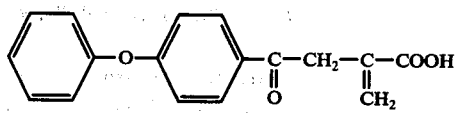

Empirical formula: $C_{17}H_{14}O_4$
Molecular weight: 282.3
White crystals
Melting point: 150° C
Plate chromatography:
 -support: silica gel
 -solvent: acetic acid/dioxane/benzene 2/8/90
 -development: ultraviolet lamp
 -Rf: 0.45
Solubility properties: the sodium salt is 10% soluble in water; the acid is insoluble. It is 3% soluble in ethyl alcohol, 1% in propylene glycol, 10% in acetone, 5% in chloroform, and 50% in NN dimethyl formamide.

EXAMPLE 5.

2-methylene 4-oxo 4-(phenyl-4'-para bromo phenyl) butyric acid ($R_1 =$ Br—⟨phenyl⟩—) (F 1378)

Using tetrachlorethane as solvent and 4-bromo biphenyl as substrate, on itaconic anhydride for 20 hours at room temperature and 4 hours reflux of the solvent, after the customary treatment, there is quantitatively recovered the derivative

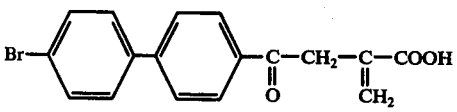

Empirical formula: $C_{17}H_{13}BrO_3$
Molecular weight: 345.2
Beige crystals
Decomposition point: 190° C
Plate chromatography:
 -solvent: silica gel
 -solvent: acetic acid/dioxane/benzene 2/8/90
 -development: ultraviolet lamp
 -Rf: 0.41 (presence of an isomer at 0.35)
Solubility properties: insoluble in water. 1% soluble in ethyl alcohol, 25% in N-methyl pyrrolidone

EXAMPLE 6.

2-methylene 4-oxo-4(4'-ortho chloro phenyl phenyl) butyric acid ($R_1 =$ 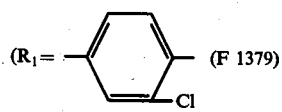) (F 1379)

By the same procedure as previously but using 2-chloro biphenyl as substrate, there is obtained

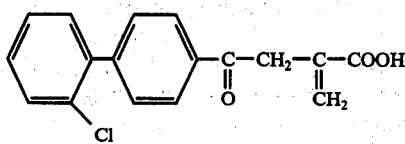

Empirical formula: $C_{17}H_{13}ClO_3$
Molecular weight: 300.7
White crystals
Decomposition point: 200° C
Plate chromatography:
    -support: silica gel
    -solvent: acetic acid/dioxane/benzene 2/8/90
    -development: ultraviolet lamp
    -Rf: 0.42

Solubility properties: insoluble in water. Soluble 25% in NN dimethyl acetamide; 20% in dimethyl sulfoxide; and 1% in ethyl alcohol.

EXAMPLE 7.

2-methylene 4-oxo 4-fluorophenyl butyric acid ($R_1 = F$) (F 1376)

The fluorobenzene is used both as solvent and as substrate.
There is obtained in a yield of 80%:

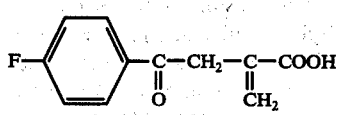

Empirical formula: $C_{11}H_9FO_3$
Molecular weight: 208.2
Light beige crystals
Instantaneous melting point on Kofler block: 109° C.
Plate chromatography:
    -support: silica gel
    -solvent: acetic acid/dioxane/benzene 2/8/90
    -development: ultraviolet lamp
    -Rf: 0.41

Solubility properties: insoluble in water. 20% soluble in ethyl alcohol and 10% soluble in propylene glycol.

EXAMPLE 8.

2-methylene 4-oxo 4-(para phenyl phenyl) butyric acid (F 1377)

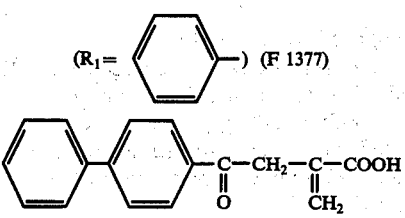

A suspension of 147 g (1.1 mole) of finely crushed aluminum chloride in 200 ml of dried tetrachlorethane is agitated at room temperature in a one liter reactor. A solution formed of 56 g (0.5 mole) of itaconic anhydride and 77 g (0.5 mole) biphenyl in 300 ml of dry tetrachlorethane is added slowly over the course of two hours to the above suspension, with mechanical agitation.

The temperature of the reaction mixture is stabilized at 35°–40° C upon the addition. The greenish solution which forms is brought for 8 hours on an oil bath to 58°–60° C. After return to room temperature, the reaction mixture is hydrolyzed in 400 ml of concentrated hydrochloric acid mixed with 1500 g of crushed ice. It is allowed to return to room temperature with agitation whereupon the reaction mixture is set aside overnight.

The acid aqueous phase is decanted and the organic phase is washed several times with water to a pH of 6–7.

The keto acid crystals formed in suspension in the tetrachlorethane are filtered and then centrifuged.

The crystals are recrystallized from 700 ml of dioxane; 99 g of white crystals are recovered (yield 75%) of a product having the formula

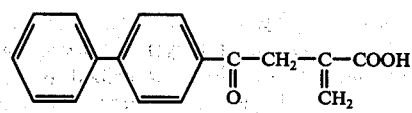

which is identified by the following analytical properties:
Empirical formula: $C_{17}H_{14}O_3$
Molecular weight: 266.3
Light beige crystals
Melting point: 208° C
Plate chromatography:
    -support: silica gel
    -solvent: acetic acid/dioxane/benzene 2/8/90
    -development: ultraviolet lamp.
    -Rf: 0.43

Solubility properties: insoluble in water even in the form of sodium salt, insoluble in ether and propylene glycol. 15% soluble in N-methyl pyrrolidone and 10% soluble in dimethyl sulfoxide.

B. Derivatives of the formula

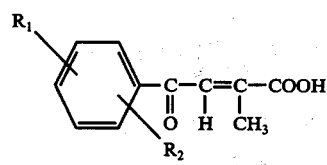

are obtained from the preceding derivatives by a transposition of the double bond in ether phase for instance in the presence of triethylamine. By way of example but not of limitation, we shall describe the derivative for which $R_1 = H$.

EXAMPLE 9.

2-methyl 4-oxo 4-phenyl 2-butenoic acid (F 1351)

Empirical formula: $C_{11}H_{10}O_3$
Molecular weight: 190.2
Yellow Crystals
Instantaneous melting point: 100° C.
Plate chromatgraphy:
    -support: silica gel
    -solvent: acetic acid/dioxane/benzene 2/8/90
    -development: ultraviolet lamp
    -Rf: 0.36

Solubility properties: the sodium salt is 1% soluble in water, the acid is 5% soluble in ethanol and 3% in propylene glycol. By transposition of the double bond there were also obtained the acids:

-2-methyl 4-oxo 4-(p-phenyl phenyl) 2-butenoic acid
-2-methyl 4-oxo 4-p-fluorophenyl 2-butnoic acid
-2-methyl 4-oxo 4-(4'-chlorophenyl phenyl) 2-butenoic acid
-2-methyl 4-oxo 4-(4'-p-bromophenyl phenyl) 2-butenoic acid
-2-methyl 4-oxo 4-(p-chlorophenyl) 2-butenoic acid
-2-methyl 4-oxo 4-(p-phenoxy phenyl) 2-butenoic acid

EXAMPLE 10.

2-methyl 4-oxo 4-(4'-o-chlorophenyl phenyl) 2-butenoic acid (F 1439)

$R_1$ = halophenyl
$R_2$ = H
$R_3$ = $CH_3$
$R_4$ = OH

A suspension of 30 g (0.1 mole) of 2-methylene 4-oxo 4-(4'-orthochlorophenyl phenyl) 2-butyric acid (F 1379), a product produced and described in our Example 6), in 300 ml of dry ether is agitated for 70 hours at 25° C with 85 ml ($\approx$ 0.6 mole) of triethylamine. 300 ml of water is added to the reaction mixture and the phases are separated. The reddish ether phase is rinsed with 100 ml of water.

The aqueous phases are combined and acidified on an ice bath with concentrated hydrochloric acid.

The crystals which form are agitated for half an hour and then filtered and washed with water.

The centrifuged crystals are recrystallized from a mixture of ethyl alcohol and water. 18 g of product are recovered. Yield 60%.

The product obtained has the formula:

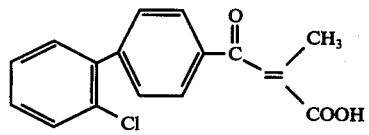

Empirical formula: $C_{17}H_{13}ClO_3$
Molecular weight: 300.74
Melting point: 196° C
Yellow crystals
Plate chromatography:
 -support: silica
 -solvent: acetic acid/dioxane/benzene 2/8/90
 -development: ultraviolet lamp
 -Rf: 0.43

Solubility properties: insoluble in water. 20% soluble in NN-dimethyl acetamide, 25% soluble in N-methyl pyrrolidone. Soluble in ether and in chloroform.

EXAMPLE 11.

2-methylene 4-oxo 4-(4'-o-chlorophenyl phenyl) methyl butyrate (F 1440)

$R_1$ = halophenyl
$R_2$ = H
$R_3$ = methylene
$R_4$ = alkoxy

To a suspension of 36 g (0.12 mole) of F 1379 in 300 ml of anhydrous acetone there are added 30.2 g (0.24 mole) of methyl sulfate diluted in 50 ml of acetone and then 20.2 g (0.24 mole) of sodium bicarbonate. The heterogeneous mixture is brought to the reflux temperature of the acetone for 12 hours. After return to room temperature, the sodium salt formed is eliminated by filtration over fritted glass and rinsed with 100 ml of acetone.

The acetone filtrate is concentrated under vacuum with a rotavapor at a temperature of 30° C. The residual oil is taken up in 300 ml of methylene chloride and treated twice with 200 ml of a 5% solution of $NaHCO_3$. It is then washed with water until neutral.

The organic phase is dried overnight over anhydrous sodium sulfate, then filtered and evaporated to dryness.

The residue is recrystallized from 60 ml of boiling methyl alcohol.

27 g recovered (yield 76%) of the product of the following formula:

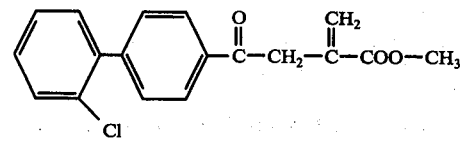

Empirical formula: $C_{18}H_{15}ClO_3$
Molecular weight: 314.77
Melting point: 85° C
Light yellow crystals
Plate chromatography:
 -support: silica
 -solvent: acetic acid/dioxane/benzene 2/8/90
 -development: ultraviolet lamp
 -Rf: 0.8

Solubility properties: insoluble in water 60% soluble in NN dimethylacetamide and in N-methyl pyrrolidone.

Corresponding other alkyl esters, especially those having up to and including eight carbon atoms, such as ethyl, butyl and octyl, are obtained by conventional esterification procedure, as are the corresponding haloalkyl such as chloroethyl, hydroxyalkyl such as hydroxypropyl, and glyceryl esters.

EXAMPLE 12.

2.(methyl 4-oxo 4-(4'-orthochlorophenyl phenyl) N(meta trifluoromethyl phenyl) 2-butenamide (F 1441)

$R_1$ = halophenyl; $R_2$ = H; $R_3$ = $CH_3$;

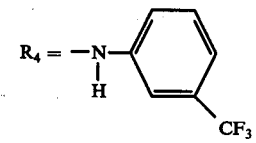

a. Preparation of the acid chloride

The acid chloride is freshly prepared from 0.125 mole of the acid (F 1439) described in Example 10 and from 0.13 mole of $PCl_5$ in 300 ml of cyclohexane.

It is heated for 1 hour under reflux and then concentrated under vacuum; 25 g of crystals of acid chloride are recovered.

b. Preparation of the amide

To a solution of 11 g (0.068 mole) of $\alpha\alpha\alpha$-trifluoro-m-toluidine and 5.4 g (0.068 mole) of pyridine in 50 ml of benzene there is slowly added, while icing, a solution of 22.4 g (0.069 mole) of previously prepared acid chloride in 250 ml of benzene. After agitating overnight at room temperature, the reaction mixture is brought to 55° C for two and a half hours. After cooling, the mixture is taken up in 250 ml of ethyl acetate and then washed with water.

The organic phase is treated thereupon with a 5% aqueous solution of hydrochloric acid and then with 5% NaHCO₃ and then washed with water until neutral.

The organic phase is evaporated and the residue obtained is recrystallized from isopropyl ether.

17 g of product (Δ 56%) are recovered having the following formula:

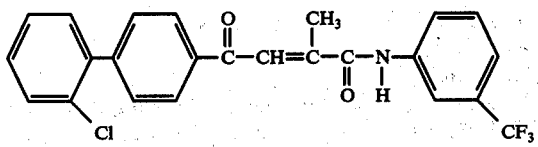

Empirical formula: C$_{24}$H$_{17}$ClF$_3$NO$_2$
Molecular weight: 443.85
White crystals
Melting point: 179° C
Plate chromatography:
 -support: silica
 -solvent: acetic acid/dioxane/benzene 2/8/90
 -development: ultraviolet lamp
 -Rf: 0.58

Solubility properties: insoluble in water, 6% soluble in alcohol.

EXAMPLE 13.

2-methyl 4-oxo 4-phenyl N(m-trifluoromethyl phenyl) 2-butenamide (F 1442)

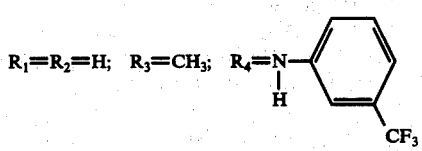

a. Preparation of the acid chloride

To a suspension of 30.3 g (0.158 mole) of 2-methyl 4-oxo 4-phenyl 2-butenoic acid (F 1351), a product described and produced in our Example 9), in 200 ml of dry cyclohexane 36.2 g (0.174 mole) of PCl$_5$ are slowly added with a spatula.

The reaction mixture is brought to the reflux temperature of the cyclohexane for one and a half hours.

After return to room temperature, the insoluble matter is filtered off. The cyclohexane and the POCl$_3$ formed is evaporated with a rotovapor under a high vacuum.

A viscous red oil is recovered which is used in crude form.

b. Preparation of the amide 32.7 g of the acid chloride previously obtained are dissolved in 30 ml of methylene chloride. The solution is iced and 24.2 g (0.15 mole) of meta-trifluoromethyl aniline and 12.4 g (0.156 mole) of pyridine dissolved in 50 ml of CH$_2$Cl$_2$ are added drop by drop.

The reaction mixture is allowed to return to room temperature, it being maintained under strong agitation for 24 hours.

It is then brought to 55° C for 45 minutes. After cooling, the amide of the following formula is recovered in the customary manner:

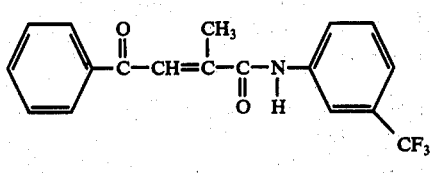

Empirical formula: C$_{18}$H$_{14}$F$_3$NO$_2$
Molecular weight: 333.31
Melting point: 90° C
Yellow crystals
Plate chromatography:
 -support: silica
 -solvent: acetic acid/dioxane/benzene 2/8/90
 -development: ultraviolet lamp and iodine
 -Rf: 0.73

Solubility properties: insoluble in water. 30% soluble in alcohol of 95° GL, 40% soluble in NN dimethyl acetamide and N-methyl pyrrolidone.

EXAMPLE 14.

N-(4-phenyl 4-oxo 2-methyl 2-butenoyl)morpholine (F 1443)

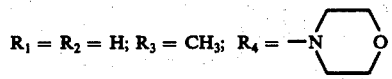

Using the acid chloride described in Example 13 and the morpholine as amine, there is recovered after the customary treatment:

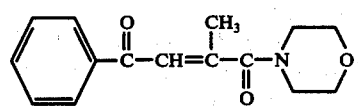

Empirical formula: C$_{15}$H$_{17}$NO$_3$
Molecular weight: 259.3
Melting point: 156° C
White crystals
Plate chromatography:
 -support: silica
 -solvent: acetic acid/dioxane/benzene 4/15/90
 -development: ultraviolet lamp and iodine
 -Rf: 0.58

Solubility properties: insoluble in water. 1.5% soluble in alcohol of 95° GL, 5% soluble in NN-dimethyl acetamide and N-methyl pyrrolidone.

EXAMPLE 15.

2-methyl 4-oxo 4-(4'-phenyl phenyl) 2-butenoic acid (F 1448) R$_1$ = phenyl; R$_2$ = H; R$_3$ = CH$_3$; R$_4$ = OH The 2-methylene 4-oxo 4-(para phenyl phenyl) butyric acid (F 1377), a product produced and described in our Example 8), is treated with triethylamine by a process similar to the preparation of F 1439 described in Example 1.

The acid of the following formula is obtained:

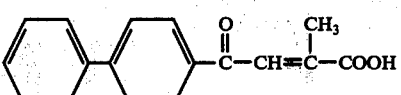

Empirical formula: $C_{17}H_{14}O_3$
Molecular weight: 266.3
Light yellow crystals
Melting point: 182° C
Plate chromatography:
- support: silica
- solvent: acetic acid/dioxane/benzene 4/25/90
- development ultraviolet lamp
- Rf.: 0.61

Solubility properties: insoluble in water. 1% soluble in alcohol, 25% soluble in NN-dimethyl acetamide and 20% soluble in N-methyl pyrrolidone.

EXAMPLE 16.

2-methylene 4-oxo 4-(4' p-chlorophenyl phenyl) butyric acid (F 1449) $R_1$ = halophenyl; $R_2$ = H; $R_3$ = methylene; $R_4$ = OH By a process similar to that used for the preparation of the F 1379 described and produced in our Example 6, but using 4-chloro biphenyl as substrate, there is obtained:

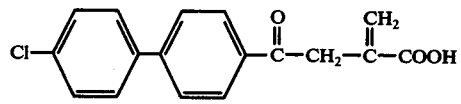

Empirical formula: $C_{17}H_{13}ClO_3$
Molecular weight: 300.7
White crystals
Melting point: 192° C
Plate chromatography:
- support: silica gel
- solvent: acetic acid/dioxane/benzene 2/8/90
- development: ultraviolet lamp
- Rf: 0.43

Solubility properties: insoluble in water, 1% soluble in absolute alcohol; 30% soluble in NN-dimethyl acetamide and N-methyl pyrrolidone.

EXAMPLE 17.

2-methylene 4-oxo 4-naphthalene butanoic acid (F 1494)

$R_1$ and $R_2$ form the benzene ring
$R_3$ is methylene
$R_4$ = OH

By a process similar to that used for the preparation of the F 1379, described and produced in our Example 6), but using naphthalene as substrate, there is obtained

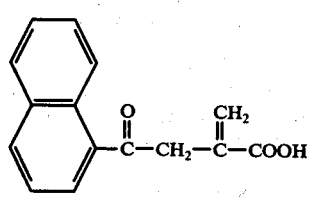

Empirical formula: $C_{15}H_{12}O_3$
Molecular weight: 240.26
White crystals
Melting point: 142° C
Plate chromatography:
- support: silica gel
- solvent: acetic acid/dioxane/benzene 2/8/90
- development: iodine
- Rf: 0.36

Solubility properties: insoluble in water. 3% soluble in alcohol, 50% soluble in N-dimethyl acetamide and N-methyl pyrrolidone.

EXAMPLE 18.

2-methylene 4-oxo 4-(1'-2'-3'-4'-tetrahydronaphthalene) butyric acid (F 1495)

$R_1$ and $R_2$ for the cyclohexyl ring
$R_3$ = methylene
$R_4$ = OH

By a process similar to that used for the preparation of F 1379, described and produced in our Example 6), but using Tetralin as substrate there is obtained:

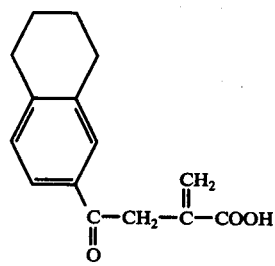

Empirical formula: $C_{15}H_{16}O_3$
Molecular weight: 244.29
White crystals
Melting point: 123° C
Plate chromatography:
- support: silica gel
- solvent: acetic acid/dioxane/benzene 2/8/90
- development: ultraviolet lamp
- Rf: 0.41

Solubility properties: insoluble in water. 8% soluble in alcohol of 95° GL, 50% soluble in N-dimethyl acetamide and N-methyl pyrrolidone.

EXAMPLE 19.

2-methylene 4-oxo 4-(4'-orthochlorophenyl phenyl) arginine butyrate (F 1496)

174 g (1 mole) of arginine are dissolved in 2.5 liters of water and 301 g (1 mole) of F 1379, a product described and produced in our Example 6), are added in small portions by spatula.

The solution is then evaporated to dryness and the residue is recrystallized from alcohol. The product of the following formula is recovered:

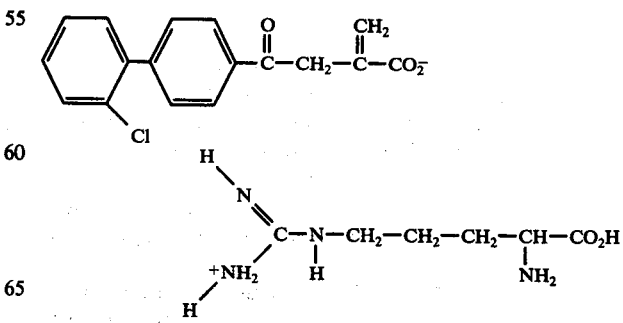

Empirical formula: $C_{23}H_{27}ClN_4O_5$

Molecular weight: 474.9
Melting point: 130° to 140° C
Yellow crystals
Solubility properties: soluble in water.

The corresponding lysine and piperazine salts are obtained according to conventional procedure in substantially the same manner.

EXAMPLE 20.

2-methylene 4-oxo 4-(3′ phenyl, 4′-methoxy phenyl)butyric acid (F 1497)

$R_1$ = phenyl; $R_2$ = alkoxy; $R_3$ = methylene; $R_4$ = OH

By a process similar to that used for the preparation of F 1379, described and produced in our Example 6), but using 2-methoxy biphenyl as substrate, there is obtained:

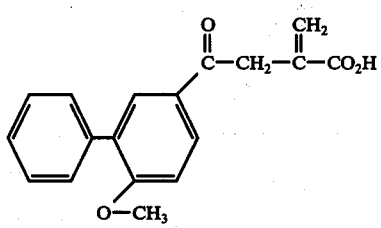

Empirical formula: $C_{18}H_{16}O_4$
Molecular weight: 296.3
White crystals
Melting point: 145° C
Plate chromatography:
 -support: silica gel
 -solvent: acetic acid/dioxane/benzene 2/8/90
 -development: ultraviolet lamp
 -Rf.: 0.36

Solubility properties: insoluble in water. 6% soluble in ethanol of 95° GL and 30% soluble in N-dimethyl acetamide.

The chemical compounds previously described were submitted to toxicity tests. The acute toxicity of certain compounds, determined by the 50% lethal dose, is reported in the following table. It was determined in mice by oral administration and was calculated in accordance with the method of MILLER & TAINTER. It is generally low and greater than 1000 mg/kg.

| Compounds | Acute toxicity in mice administered orally $LD_{50}$ in mg/kg (mortality determined 48 hours after administration) |
|---|---|
| F 1350 compound No. 2 | 2500 |
| F 1351 compound No. 9 | 1700 |
| F 1352 compound No. 3 | 1500 |
| F 1376 compound No. 7 | 1400 |
| F 1377 compound No. 8 | >2000 |
| F 1378 compound No. 5 | 1050 |
| F 1379 compound No. 6 | 1500 |
| F 1380 compound No. 4 | 700 |
| F 1439 | 2370 |
| F 1440 | >1000 |
| F 1442 | >1000 |
| F 1449 | >1000 |

The pharmacological experiments to which these new compounds were subjected made is possible to note antiinflammatory, analgetic, and hypolipemizing properties.

The antiinflammatory properties were shown by the carrageenin edema test in rats, the products having been administered orally one hour before the intrapodal injection of 0.05 ml of a 2% suspension of carrageenin; the volume of the rat's paw was measured by plethysmoscopy 3, 4 and 6 hours afterwards.

The experiment concerned for each lot about 30 lots; one lot of animals receiving only the vehicle (2 ml/100 g of Tween + water) which served for the administration of the products, constituted the control lot. The following table sets forth the results obtained:

| Lots | Number of Rats | Mean Weight | Parameters | % increase in volume of the paw at + 3 hrs | + 4 hrs | + 6 hrs | % mean variation of the volume of the paw at 3,4 and 6 hrs. |
|---|---|---|---|---|---|---|---|
| Controls 2 ml/100 g Tween + water | 10 | 185 | m s2 md | 50,1 51,43 2,3 | 49,7 40,68 2,0 | 46,0 55,33 2,3 | |
| F 1350 300 mg/kg | 10 | 185 | m s2 md Action | 34,3 137,79 3,7 −31% p <0,01 | 39,7 128,01 3,6 −20% p <0,05 | 46,1 200,99 4,5 0 | −17 |

| Lots | Number of rats | Mean Weight | Parameters | % increase in volume of the paw at + 3 hrs | + 4 hrs | + 6 hrs | Cumulative |
|---|---|---|---|---|---|---|---|
| Controls 2cc/100 g (Tween + water) | 20 | 191 | m s2 md | 58,45 159,313 2,8 | 65,0 132,315 2,6 | 67,45 100,155 2,3 | 190,9 |
| F 1379 50 mg/kg | 20 | 190 | m s2 md Action | 24,40 72,042 2,0 −58,2% p<0,00 | 34,35 128,239 2,5 −47,0% p<0,001 | 47,40 129,200 2,5 −29,7% p<0,001 | 106,1 −44,4% |
| F 1379 100 mg/kg | 19 | 194 | m s2 md | 18,74 66,538 1,9 | 26,05 120,274 2,5 | 38,8 233,286 3,5 | 83,6 |

-continued

|  |  |  | Action | −67,9% <br> p<0,001 | −59,9% <br> p<0,001 | −42,5% <br> p<0,001 | −56,2% |
|---|---|---|---|---|---|---|---|
| F 1379 <br> 200 mg/kg | 20 | 198 | m <br> s2 <br> md <br> Action | 19,6 <br> 118,357 <br> 2,4 <br> −66,4% <br> p<0,001 | 25,1 <br> 157,463 <br> 2,8 <br> −61,3% <br> p<0,001 | 32,8 <br> 241,642 <br> 3,5 <br> −51,3% <br> p<0,001 | 77,5 <br><br><br> −59,4% |
| Controls | 10 | 180 | m <br> s2 <br> md | 70,9 <br> 41,211 <br> 2,0 | 66,5 <br> 28,277 <br> 1,7 | 66,1 <br> 44,988 <br> 2,1 | 203,5 |
| F 1379 <br> 30 mg/kg | 10 | 180 | m <br> s2 <br> md <br> Action | 58,4 <br> 51,600 <br> 2,3 <br> −17,6% <br> p<0,001 | 60,1 <br> 37,877 <br> 1,0 <br> −9,6% <br> p<0,05 | 61,1 <br> 80,100 <br> 2,8 <br> −7% <br> p>0,01 | 179,6 <br><br><br> −11,7% |

| Lots | Number of Rats | Mean Weight | Parameters | % increase in volume of the paw at | | | % mean variation of the paw at 3, 4 and 6 hrs. |
|---|---|---|---|---|---|---|---|
|  |  |  |  | + 3 hrs | + 4 hrs | + 6 hrs |  |
| Controls <br> 2 ml/100 g <br> Tween + <br> water | 10 | 185 | m <br> s2 <br><br> md | 50,1 <br> 51,43 <br><br> 2,3 | 49,7 <br> 40,68 <br><br> 2,0 | 46,0 <br> 55,33 <br><br> 2,3 |  |
| F 1351 <br> 300 mg/kg | 10 | 185 | m <br> s2 <br><br> md <br> Action | 29,7 <br> 47,79 <br><br> 2,2 <br> −41% <br> p<0,01 | 33,8 <br> 63,07 <br><br> 2,5 <br> −32% <br> p<0,01 | 40,6 <br> 195,16 <br><br> 4,4 <br> −12% <br> p>0,05 | −28 |
| F 1352 <br> 300 mg/kg | 9 | 190 | m <br> s2 <br><br> md <br> Action | 35,8 <br> 102,69 <br><br> 3,4 <br> −28% <br> p<0,01 | 37,9 <br> 137,61 <br><br> 3,9 <br> −24% <br> p<0,05 | 37,3 <br> 248,50 <br><br> 5,2 <br> −19% <br> p>0,05 | <23,6 |
| Controls <br> 2 ml/100 g <br> Tween + <br> water | 10 | 180 | m <br> s2 <br><br> md | 61,6 <br> 43,60 <br><br> 2,1 | 60,4 <br> 50,26 <br><br> 2,4 | 57,1 <br> 41,87 <br><br> 2,0 |  |
| F 1376 <br> 300 mg/kg <br> P.O.-1 h | 10 | 175 | m <br> s2 <br><br> md <br> Action | 50,8 <br> 40,17 <br><br> 2,0 <br> −17% <br> p<0,01 | 51,5 <br> 32,50 <br><br> 1,8 <br> −15% <br> p<0,05 | 54,8 <br> 47,95 <br><br> 2,2 <br> −4% <br> p>0,05 | −12 |
| F 1378 <br> 300 mg/kg <br> P.O.-1 h | 10 | 180 | m <br> s2 <br><br> md <br> Action | 45,4 <br> 20,26 <br><br> 1,4 <br> −26% <br> p<0,01 | 47,9 <br> 24,10 <br><br> 1,5 <br> −21% <br> p<0,01 | 52,4 <br> 46,93 <br><br> 2,2 <br> −8% <br> p>0,05 | −18,3 |
| F 1380 <br> 200 mg/kg <br> P.O.-1 h | 10 | 175 | m <br> s2 <br><br> md <br> Action | 50,3 <br> 49,12 <br><br> 2,2 <br> −18% <br> p<0,01 | 52,8 <br> 18,17 <br><br> 1,3 <br> −12% <br> p<0,05 | 55,6 <br> 30,26 <br><br> 1,7 <br> −3% <br> p<0,05 | −11 |

Carrageenin edema

| Lots | Number of Rats | Mean Weight | Parameters | % increase in volume of the paw at | | | % mean variation of the volume of the paw at 3,4 and 6 hrs. |
|---|---|---|---|---|---|---|---|
|  |  |  |  | 3 hrs | 4 hrs | 6 hrs |  |
| Controls | 30 | 170 | m <br> s2 <br> md | 60 <br> 108,616 <br> 2 | 59 <br> 86,116 <br> 2 | 56 <br> 114,685 <br> 2 |  |
| F 1439 <br> 75 mg/kg | 30 | 172 | m <br> s2 <br> md <br> % var. | 38 <br> 89,223 <br> 2 <br> −36 <br> p<0,01 | 40 <br> 77,058 <br> 2 <br> −33 <br> p<0,01 | 40 <br> 113,688 <br> 2 <br> −28 <br> p<0,01 | −32 |
| F 1440 <br> 75 mg/kg | 30 | 169 | m <br> s2 <br> md <br> % var. | 47 <br> 123,961 <br> 2 <br> −22 <br> p<0,01 | 50,5 <br> 130,185 <br> 2,083 <br> −15 <br> p<0,01 | 51 <br> 169,840 <br> 2,379 <br> −9 <br> p>0,05 | −15 |
| F 1442 <br> 75 mg/kg | 30 | 167 | m <br> s2 <br> md | 50 <br> 90,809 <br> 2 | 51 <br> 73,167 <br> 1,5 | 49 <br> 49,126 <br> 1 | −13 |

-continued

| | | | | % var. | −16<br>p<0,01 | −14<br>p<0,01 | −11<br>p<0,05 | |
|---|---|---|---|---|---|---|---|---|
| F 1449<br>75 mg/kg | 30 | 162 | m<br>s2<br>md<br>% var. | | 42<br>132,723<br>2<br>−29<br>p<0,01 | 45<br>124,488<br>2<br>−24<br>p<0,01 | 44,5<br>121,978<br>2<br>−20<br>p<0,01 | −24 | m = mean  s2 = variance  md = mean deviation  p = precision

The analgetic properties were shown in a male mouse of a weight of close to 22 g by the "writhing test" method, that is to say based on the writhings induced by acetic acid. The administration of the compounds is effected by mouth at the time t. It is followed by the intraperitoneal injection of 10 mg/kg of 0.75% acetic acid at the time $t + 50$ min. The determination of the writhings is effected from $t + 60$ min. to $t + 70$ min. The vehicle used for the administration of the products is a 5% solution of Tween 80 in 0.9% NaCl which will serve as control. The results thus obtained are set forth in the following table:

| Compound | Dose mg/kg | No. of Animals | Mean No. of Writhings | Mean Deviation | % Decrease |
|---|---|---|---|---|---|
| Control (vehicle) | 25 ml/kg | 15 | 44,6 | 4,8 | — |
| F 1350 | 200 mg/kg | 15 | 25,7 | 6,5 | 42,3 % |
| F 1351 | 200 mg/kg | 15 | 28,0 | 4,5 | 48,2 % |
| F 1352 | 200 mg/kg | 15 | 26,6 | 4,0 | 40,3 % |
| Control (vehicle) | 25 ml/kg | 30 | 39,0 | 3,8 | — |
| F 1379 | 200 mg/kg | 20 | 31,8 | 2,7 | 18,4 % |
| acetylsalicylic acid | 200 mg/kg | 30 | 24,7 | 3,2 | 36,6 |

The analgetic properties of certain compounds were shown in mice by the "writhing test" method, that is to say with reference to the writhings induced by phenylbenzoquinone. The administration of the product is effected orally at time t; it is followed by the intraperitoneal injection of 0.2% phenylbenzoquinone at $t + 30$ min. The determination of the writhings is effected from $t + 35$ min. to $t + 40$ min. One lot of animals receiving only the vehicle (5% Tween 80 in 0.9% NaCl) serves as control. The results are set forth in the following table:

| Compound | Dose mg/kg | Number of Animals | Mean No. of Writhings | Mean Deviation | % Decrease |
|---|---|---|---|---|---|
| Control (vehicle) | 25 ml/kg | 20 | 25,5 | 2,4 | |
| F 1377 | 300 | 20 | 8,00 | 1,4 | 68,6 |
| Control (vehicle) | 25 ml/kg | 18 | 33,05 | 2,8 | |
| F 1449 | 200 | 20 | 27,4 | 2,7 | 17 |

The hypocholesterolemizing properties were observed for compounds of the invention according to standard test procedure employing rats maintained upon a normal diet, and then subjected to oral administration of the compounds for 4 consecutive days. One lot of rats served as control.

The sampling was effected on the 5th day after 16 hours fasting, by cardiac puncture and the total blood cholesterol determination was effected by the Liebermann-Burchardt colorimetric method.

The results for certain compounds in the series are set forth in the following table.

| Compound | No. of rats | Parameters | | | % Variation of the Cholesteral |
|---|---|---|---|---|---|
| | | M | S2 | MD | |
| Control | 10 | 0,80 | 0,009 | 0,03 | |
| F 1377<br>200 mg/kg | 10 | 0,61 | 0,017 | 0,042 | −23,75<br>P<0,01 |
| Control | 10 | 1,06 | 0,009 | 0,03 | |
| F 1439<br>300 mg/kg | 10 | 0,67 | 0,009 | 0,03 | −36,8<br>P<0,01 |
| F 1379<br>300 mg/kg | 11 | 0,62 | 0,007 | 0,024 | −41,8<br>P<0.01 |

This hypocholesterolemizing effect is accordingly utilized in the treatment of a subject, i.e., living animal body, i.e., in a method of reducing blood cholesterol, which comprises administering, by any suitable route, preferably orally, to a subject in need of blood cholesterol reduction, e.g., for prophylactic or ameliorative purposes, an effective cholesterol reducing amount of a compound of the invention, preferably in the form of the free acid or a pharmaceutically-acceptable salt thereof, and preferably in the form of a pharmaceutical composition together with a pharmaceuticallyacceptable carrier, all as further disclosed hereinafter.

After having made certain of a tolerance compatible with therapeutic application, clinical tests were carried out in the case of some of the compounds forming the object of the invention. They were applied in the field of the prevention and treatment of inflammatory syndromes which appear, for instance, in cases of inflammatory polyarthritis, rheumatoid arthritis, osteoarthritis, lumbago, injuries to the locomotor apparatus, but also in the treatment of atherosclerosis. Within the clinical tests carried out, especially in rheumatology and traumatology, the compounds were used either in their free acid state or in the state of a pharmaceutically acceptable salt (salt of sodium, potassium, lithium, arginine, piperizine, dimethylamino ethanol, etc.). They were administered orally in the form of tablets, capsules or pills having a dose of 50 to 1000mg per unit. Other forms may be used for general administration and for local applications.

Depending on the results which it is desired to obtain they were administered in oral form (tablets, sugar-coated pills, capsules), parenteral form, rectal form or local form. The compounds claimed can be used alone or in combination with other active principles useful for the treatment.

By way of illustration and not of limitation, a few formulas for pharmaceutical preparations containing compounds forming the object of the invention alone or combined with other active principles useful for the complete treatment of the ailment concerned are given below:

| 1) Coated tablets | |
|---|---|
| F 1379 | 100 mg |
| excipient qsp | 1 enteric coated tablet |
| or | |
| F 1439 | 100 mg |
| excipient qsp | 1 tablet |
| 2) Suppositories | |
| F 1379 | 200 mg |
| N-butylhyoscine bromide | 10 mg |
| excipient qsp | 1 suppository of 2 g |
| or | |
| F 1449 | 100 mg |
| Noramidopyrine methane sulfonate | 250 mg |
| excipient qsp | 1 adult suppository |
| 3) Cream | |
| F 1379 | 2 g |
| Mephenesine | 10 g |
| excipient qsp | 100 g |
| 4) Tablets | |
| F 1377 | 100 mg |
| Noramidopyrine methane sulfonate | 200 mg |
| excipient qsp | 1 tablet |
| or | |
| F 1351 | 300 mg |
| Meprobamate | 250 mg |
| excipient qsp | 1 tablet |
| 5) Solution for injection | |
| F 1379 sodium salt | 300 mg |
| water for injection | 2 ml |
| or | |
| F 1496 | 300 mg |
| Dibencozide, lyophilized | 3 mg |
| water for injection | 5 ml |

From the foregoing, it is apparent that the compounds of the present invention are active antiinflammatory, analgetic, and hypocholesteremic compounds. As such, they may be utilized either per se or preferably in the form of pharmaceutical compositions together with pharmaceutic diluents, carriers, or adjuvants, according to the customary procedure in the art. They may, in this manner, be embodied into pharmaceutical compositions, comprising an effective antiinflammatory or analgetic amount of the compound together with a pharmaceuticallyacceptable carrier. They may be administered in the form of such pharmaceutical compositions wherein the amount of active ingredient is preferably between about 50 and 1000 mg. per unit, depending upon the patient involved and the exact syndrome being treated, depending of course upon the judgment of the physician or veterinarian in charge, body weight of the patient, et cetera. The daily regimen is accordingly one to four of such unit dosages as previously mentioned, for prophylactic or ameliorative treatment of the exact condition involved, whether inflammation, pain, or a tendency toward excess blood cholesterol. In the treatment of inflammatory or pain syndromes, the compounds or compositions are administered to a subject suffering therefrom in an effective antiinflammatory or analgetic amount. When the compounds or compositions are employed for their hypocholesterolemizing effect, they are administered to a subject in need of cholesterol reduction, particularly blood cholesterol reduction, in an effective cholesterol-reducing amount. For all uses, the compounds or compositions are preferably administered orally, and preferably are administered in the form of the free acid or a pharmaceutically acceptable salt thereof. In all cases, the compounds or compositions are preferably, although not necessarily, administered orally. All of the usual diluents, carriers, or adjuvants may be employed to facilitate administration of the compounds of the present invention. The compounds may obviously be administered in combination with other active ingredients, in accord with standard practice in the art.

Of the compounds disclosed in this application, the preferred compounds are those wherein $R_3$ is methylene, $R_4$ is selected from the group consisting of hydroxy and methoxy, $R_2$ is selected from the group consisting of hydrogen and methoxy, and $R_1$ is selected from the group consisting of chlorine, fluorine, phenoxy, phenyl, and halophenyl. Innumerable pharmaceutically-acceptable salts are readily available and conventionally prepared, such as those mentioned hereinbefore. Salts with alkali and alkaline-earth metals, amino acids such as arginine and lysine, or amines such as diloweralkylamino alkanols and the like are preferred, as are salts with piperazine and the like. Of the preferred compounds mentioned above, those which are free acids or pharmaceuticallyacceptable salts thereof, wherein $R_1$ is phenyl or ortho-halophenyl, especially those compounds wherein $R_3$ is methylene, are especially preferred, compounds of the types F 1377 and F 1379 and the like being particularly preferred from the standpoint of their hypocholesterolemizing action.

It is to be understood that the invention is not to be limited to the exact details of operation or exact compounds, compositions, methods, or procedures shown and described, as obvious modifications and equivalents will be apparent to one skilled in the art.

We claim:
1. 2-methylene 4-oxo 4-(4'-orthochlorophenyl phenyl) butyric acid.

* * * * *